United States Patent [19]
Powell et al.

[11] Patent Number: 5,856,593
[45] Date of Patent: Jan. 5, 1999

[54] PROCESS FOR THE PRODUCTION OF FLUORINE CONTAINING OLEFINS

[75] Inventors: Richard Llewellyn Powell, Bunbury; Andrew Paul Sharratt, Middlewich, both of United Kingdom

[73] Assignee: Imperial Chemical Industries PLC, Millbank, England

[21] Appl. No.: 776,644

[22] PCT Filed: Jul. 31, 1995

[86] PCT No.: PCT/GB95/01799

§ 371 Date: Feb. 4, 1997

§ 102(e) Date: Feb. 4, 1997

[87] PCT Pub. No.: WO96/05157

PCT Pub. Date: Feb. 22, 1996

[30] Foreign Application Priority Data

Aug. 8, 1994 [GB] United Kingdom .................... 9416009
Nov. 25, 1994 [GB] United Kingdom .................... 9423778

[51] Int. Cl.$^6$ ...................................................... C07C 17/25
[52] U.S. Cl. ............................................. 570/156; 570/158
[58] Field of Search ...................................... 570/156, 158

[56] References Cited

U.S. PATENT DOCUMENTS 2,599,631 12/1952 Harmon .
2,774,799 12/1956 Mantell et al. .......................... 570/156
3,432,562 3/1969 Gardner ................................. 570/156
3,636,172 1/1972 Gardner .

FOREIGN PATENT DOCUMENTS 0 406 748 1/1991 European Pat. Off. .
406748 1/1991 European Pat. Off. .
2 710 054 3/1995 France .

Primary Examiner—Alan Siegel

[57] ABSTRACT

Production of trifluoroethylene from 1,1,1,2-tetrafluoroethane and/or 1,1,2,2-tetrafluoroethane in a heated reaction zone in the presence of a Lewis acid catalyst.

14 Claims, No Drawings

PROCESS FOR THE PRODUCTION OF FLUORINE CONTAINING OLEFINS

This application is a 371 of PCT/GB95/01799 filed Jul. 31, 1995.

The present invention relates to a process for the production of a fluorine containing olefin and more particularly to a process for the production of trifluoroethylene.

According to the present invention there is provided a process for the production of a fluorine containing olefin which process comprises passing a gaseous feed comprising a saturated hydrohalocarbon reactant having a fluorine substituent and one or more further halogen substituents through a heated reaction zone in which there is contained a Lewis acid catalyst.

In the process of the present invention, a gaseous feed comprising a saturated hydrohalocarbon reactant having a fluorine substituent and one or more further halogen substituents is passed through a heated reaction zone where it is subjected to a dehydrohalogenation reaction in the presence of a Lewis acid catalyst so as to yield the desired fluorine containing olefin.

The process of the present invention may be used to prepare a variety of fluorine containing olefins, but is particularly concerned with the production of fluorine containing ethylenes and more specifically with the production of trifluoroethylene. Fluorine containing ethylenes are prepared by subjecting a hydrohaloethane starting material containing a fluorine substituent and one or more further halogen substituents to the process of the present invention. The one or more further halogen substituents contained in the hydrohaloethane may be fluorine, chlorine, bromine and/or iodine atoms, but will preferably be fluorine and/or chlorine atoms and more preferably will be exclusively fluorine atoms. When the process of the present invention is being used to prepare trifluoroethylene, the hydrohaloethane starting material is preferably one of 1,1,1,2-tetrafluoroethane (hereinafter R-134a) and 1,1,2,2-tetrafluoroethane (hereinafter R-134), and more preferably is R-134a.

The heated reaction zone may be provided by any suitably configured reactor vessel. Conveniently, the heated reaction zone is provided by a heated tube reactor. The reactor vessel should, of course, be made of a thermally conductive material which is stable, i.e. will not decompose or melt, at the elevated temperatures and under the chemical environment prevailing during operation of the process. Thus, the reactor vessel may, for example, be made of carbon, graphite or a conductive metal or metal alloy such as nickel and its alloys. It has been found that reactor vessels made of nickel are particularly efficacious in the process of the present invention.

Suitable Lewis acid catalysts for the present process include chromia ($Cr_2O_3$) and materials comprising chromia which has been doped with a metal, possibly in the form of a metal compound. Suitable metals for doping the chromia include nickel, cobalt, zinc, iron and copper, especially zinc.

Other suitable catalysts are the fluorine containing Lewis acids such as aluminium fluoride ($AlF_3$) and materials comprising a fluorine containing Lewis acid which has been doped with a metal, possibly in the form of a metal compound. Suitable metals for doping the fluorine containing Lewis acid include nickel, cobalt, zinc, iron and copper, especially iron.

Preferred catalysts are those comprising a fluorine containing Lewis acid and catalysts comprising aluminium fluoride are especially preferred. The catalyst may be compressed into pellets and used in a fixed bed or, alternatively, it may be used in particulate form in a fluidised bed. Mixtures of two or more different catalysts may also be used in the process of the present invention. The catalyst will tend to lose its activity after a time, but spent catalyst may be regenerated by heating it in air at a temperature in the range of from 500° to 1000° C., more preferably in the range of from 600° to 1000° C.

The process of the present invention is carried out at elevated temperature in a heated reaction zone. Reaction temperatures in the range of from 350° to 1200° C. are generally employed, with reaction temperatures in the range of from 350° to 1000° C. being preferred. When the process of the present invention is being used to prepare trifluoroethylene from R-134 or R-134a, then the reaction temperature employed is preferably in the range of from 350° to 800° C. and more preferably in the range of from 400° to 600° C.

The residence time for the hydrohalocarbon reactant in the reaction zone is generally in the range of from 0.01 to 100 seconds, with residence times in the range of from 0.1 to 10 seconds being preferred. When the process of the present invention is being used to prepare trifluoroethylene from R-134 or R-134a, then the residence time for the R-134 or R-134a reactant in the reaction zone is preferably in the range of from 0.1 to 7 seconds and more preferably in the range of from 0.3 to 5 seconds. In this specification, by the term residence time we mean the residence time as calculated at room temperatures and pressures (RTP) in accordance with the equation below.

$$\text{Residence time at } RTP \text{ (in seconds)} = \frac{\text{Volume of the reaction zone provided by the reactor vessel (ml)}}{\text{Volumetric fluid flow rate, i.e. the volume of fluid being fed to the reactor vessel per unit of time (ml/second)}}$$

In calculating the volumetric fluid flow rate, it is necessary to take into account all the fluids which are to be fed to the reactor vessel. The process of the present invention may, of course, be operated so that the hydrohalocarbon reactant is the only fluid being charged to the reactor vessel, in which case only the flow rate of this fluid needs to be considered. However, when the process of the present invention employs a gaseous diluent (discussed hereinafter) in addition to the hydrohalocarbon reactant, the volumetric fluid flow rate will be a measure of the total volume of diluent and hydrohalocarbon reactant (in ml) being fed to the reactor vessel per second.

Although the gaseous feed entering the reaction zone may be composed entirely, or substantially entirely, of the hydrohalocarbon reactant, it will preferably also comprise an inert diluent gas or vapour which is stable at the elevated temperatures and under the chemical environment prevailing during operation of the process. Examples of possible diluent gases/vapours include nitrogen, carbon dioxide, carbon tetrafluoride, steam and superheated steam. When superheated steam is employed as the diluent, it may be possible to achieve and maintain the desired reaction temperature without using separate heating means. The preferred diluent gas is nitrogen.

When a diluent is employed (as is preferred), the volume ratio of the diluent to the hydrohalocarbon reactant in the gaseous feed entering the reaction zone is preferably in the range of from 1:1 to 20:1, more preferably in the range of from 2:1 to 9:1 and particularly preferably in the range of from 4:1 to 9:1.

The reaction pressure employed in the process of the present invention is not normally critical and may be atmospheric, sub-atmospheric, or super-atmospheric. However, operating pressures in the region of atmospheric pressure are preferred and, in general, operation at atmospheric pressure or substantially atmospheric pressure is particularly preferred.

The heating of the reactor vessel to generate the required reaction temperature may be accomplished by any suitable heating means. For example, heating may be achieved by electromagnetic induction or by means of a furnace disposed around the reactor vessel. Furthermore, as we have previously explained, it may be possible to generate the required reaction temperature in the reaction zone using a superheated diluent gas or vapour.

When operating the process of the present invention, the hot gas stream emerging from the reactor vessel is normally quench cooled.

The crude material which is obtained from the present process may be treated and purified by conventional techniques (e.g. distillation) in order to isolate and collect the fluorine containing olefin.

Any unreacted starting material collected from the process may be recycled to the entry side of the reactor vessel and passed through the reaction zone once again in order to improve conversion.

The present invention is now illustrated but not limited with reference to the following examples all of which relate to the production of trifluoroethylene (TriFE) from 1,1,1,2-tetrafluoroethane (R-134a).

GENERAL PROCEDURE AND APPARATUS

The reactor vessel comprised a piece of nickel tubing of length 15 cms, internal diameter 0.21 cms and external diameter 0.45 cms. This reactor tube was conditioned first of all by heating it at 800° C. while passing a gaseous feed containing 90% by volume of nitrogen and 10% by volume of R-134a through the central reaction zone at a rate of 50 ml/minute. This process was continued for a total of 4 hours.

Once the conditioning process was completed, the reactor tube was ready for the experimental work. A piece of steel gauze was compressed and inserted into the reactor tube in order to retain the catalyst. The catalyst was then placed in the reactor tube and the gas feeds (nitrogen diluent and R-134a), which were controlled by means of mass flow controllers, were set and measured using a bubble flow meter. The gas feeds were thoroughly mixed together using a static mixer before being passed into the reactor tube. The reactor tube was then gradually heated to the desired reaction temperature (400° to 600° C.) using a tube furnace and while the furnace was warming up samples of the feed stream emerging from the mass flow controllers were taken and analysed in order to accurately determine the feed concentration. The gaseous product stream emerging from the reactor tube was passed through a caustic scrubber before being sampled and analysed in order to remove any hydrogen fluoride which it might contain.

When the reactor had reached the desired reaction temperature, samples of the gaseous product stream emerging from the scrubber were collected and analysed by gas chromatographic mass spectroscopy. The data obtained was used to calculate the conversion of R-134a to products and the selectivity to TriFE.

EXAMPLE 1

The above described general procedure was used to prepare TriFE from R-134a. The catalyst used was aluminium fluoride which had been previously dried by heating it to 250° C. in a stream of nitrogen for 3 hours. 0.45 g of the aluminium fluoride catalyst was loaded into the reactor tube and the flows of nitrogen and R-134a were then started and adjusted so that the gaseous feed entering the reactor tube contained 97.58% by volume of nitrogen and 2.42% by volume of R-134a. The reactor tube was initially heated to a temperature of 500° C. and during the course of the experiment this temperature was increased to 550° C. and then finally to 600° C. At each temperature, a sample of the gaseous product stream emerging from the scrubber was collected and analysed once the system had equilibrated.

The results achieved in terms of the conversion of R-134a to products and the selectivity to TriFE formation are shown in Table 1 below.

EXAMPLE 2

The above described general procedure was used to prepare TriFE from R-134a. The catalyst used was aluminium fluoride which had been previously dried by heating it to 250° C. in a stream of nitrogen for 3 hours. 0.45 g of the aluminium fluoride catalyst was loaded into the reactor tube and the flows of nitrogen and R-134a were then started and adjusted so that the gaseous feed entering the reactor tube contained 92.0% by volume of nitrogen and 8.0% by volume of R-134a. The temperature of the reactor tube was raised to 600° C. and once this temperature had been attained the time was set at zero and monitoring of the reaction process began with samples of the gaseous product stream emerging from the scrubber being collected at various times and analysed by gas chromatographic mass spectroscopy.

The results achieved in terms of the conversion of R-134a to products and the selectivity to TriFE formation at the various times are shown in Table 2 below.

EXAMPLE 3

The above described general procedure was used to prepare TriFE from R-134a. The catalyst used in Example 2 was regenerated while in situ in the reactor by heating it to 600° C. in a continuous flow of air for approximately 3 hours. At the end of the regeneration, the catalyst was allowed to cool in a flow of nitrogen. Once the catalyst had cooled, the flows of nitrogen and R-134a were started and adjusted so that the gaseous feed entering the reactor tube contained 92.0% by volume of nitrogen and 8.0% by volume of R-134a. The temperature of the reactor tube was raised to 600° C. and once this temperature had been attained the time was set at zero and monitoring of the reaction process began with samples of the gaseous product stream emerging from the scrubber being collected at various times and analysed by gas chromatographic mass spectroscopy.

The results achieved in terms of the conversion of R-134a to products and the selectivity to TriFE formation at the various times are shown in Table 3 below.

EXAMPLE 4

The above described general procedure was used to prepare TriFE from R-134a. The catalyst used was a blend of aluminium fluoride doped with iron in the form of an iron compound. The catalyst was dried prior to use by heating it to 250° C. in a stream of nitrogen for 3 hours. 0.70 g of the catalyst was loaded into the reactor tube and the flows of nitrogen and R-134a were then started and adjusted so that the gaseous feed entering the reactor tube contained 93.0% by volume of nitrogen and 7.0% by volume of R-134a. The reactor tube was initially heated to a temperature of 450° C. and during the course of the experiment this temperature was increased in stages to 475° C., 500° C. and then finally to 525° C. At each temperature, a sample of the gaseous product stream emerging from the scrubber was collected and analysed once the system had equilibrated.

The results achieved in terms of the conversion of R-134a to products and the selectivity to TriFE formation are shown in Table 4 below.

EXAMPLE 5

The above described general procedure was used to prepare TriFE from R-134a. The catalyst used was a blend of aluminium fluoride doped with iron in the form of an iron compound. The catalyst was dried prior to use by heating it to 250° C. in a stream of nitrogen for 3 hours. 0.40 g of the catalyst was loaded into the reactor tube and the flows of nitrogen and R-134a were then started and adjusted so that the gaseous feed entering the reactor tube contained 93.5% by volume of nitrogen and 6.5% by volume of R-134a. The temperature of the reactor tube was raised to 500° C. and once this temperature had been attained the time was set at zero and monitoring of the reaction process began with samples of the gaseous product stream emerging from the scrubber being collected at various times and analysed by gas chromatographic mass spectroscopy.

The results achieved in terms of the conversion of R-134a to products and the selectivity to TriFE formation at the various times are shown in Table 5 below.

EXAMPLE 6

The above described general procedure was used to prepare TriFE from R-134a. The catalyst used was a zinc on chromia catalyst (3% by weight of zinc) which had been previously dried by heating it to 250° C. in a stream of nitrogen for 3 hours. 0.50 g of the catalyst was loaded into the reactor tube and the flows of nitrogen and R-134a were then started and adjusted so that the gaseous feed entering the reactor tube contained 93.54% by volume of nitrogen and 6.46% by volume of R-134a. The reactor tube was initially heated to a temperature of 400° C. and during the course of the experiment this temperature was increased in stages to 450° C., 475° C. and then finally to 500° C. At each temperature, a sample of the gaseous product stream emerging from the scrubber was collected and analysed once the system had equilibriated.

The results achieved in terms of the conversion of R-134a to products and the selectivity to TriFE formation are shown in Table 6 below.

TABLE 1

| Temperature (°C.) | 500 | 550 | 600 |
|---|---|---|---|
| Conversion of R-134a (%) | 0.42 | 24.4 | 34.0 |
| Selectivity to TriFE (%) | 100 | 99.79 | 99.76 |

TABLE 2

| Time (minutes) | Selectivity to TriFE (%) | Conversion of R-134a (%) |
|---|---|---|
| 7 | 98.60 | 38.40 |
| 22 | 99.60 | 23.12 |

TABLE 2-continued

| Time (minutes) | Selectivity to TriFE (%) | Conversion of R-134a (%) |
|---|---|---|
| 37 | 99.29 | 23.24 |
| 52 | 99.49 | 18.30 |
| 67 | 99.38 | 16.75 |
| 82 | 98.82 | 7.38 |
| 102 | 98.99 | 13.88 |
| 117 | 98.90 | 12.49 |
| 135 | 98.90 | 12.27 |
| 157 | 98.89 | 9.29 |
| 173 | 98.76 | 8.97 |
| 190 | 98.79 | 5.84 |

TABLE 3

| Time (minutes) | Selectivity to TriFE (%) | Conversion of R-134a (%) |
|---|---|---|
| 20 | 99.29 | 22.41 |
| 49 | 99.46 | 21.07 |
| 66 | 99.53 | 16.22 |
| 95 | 99.45 | 15.94 |
| 113 | 99.49 | 10.43 |
| 142 | 99.45 | 12.03 |
| 159 | 99.42 | 12.81 |
| 189 | 99.53 | 15.67 |
| 206 | 99.62 | 12.05 |
| 244 | 99.60 | 12.80 |
| 261 | 99.61 | 13.23 |
| 291 | 99.58 | 13.65 |

TABLE 4

| Temperature (°C.) | 450 | 475 | 500 | 525 |
|---|---|---|---|---|
| Conversion of R-134a (%) | 9.07 | 13.74 | 21.92 | 4.2 |
| Selectivity to TriFE (%) | 99.01 | 99.25 | 99.44 | 98.60 |

TABLE 5

| Time (minutes) | Selectivity to TriFE (%) | Conversion of R-134a (%) |
|---|---|---|
| 18 | 99.57 | 26.28 |
| 35 | 99.57 | 26.20 |
| 53 | 99.70 | 21.04 |
| 79 | 99.74 | 25.47 |
| 109 | 99.70 | 23.79 |
| 139 | 99.62 | 24.96 |
| 159 | 99.72 | 28.24 |
| 179 | 99.28 | 24.70 |
| 194 | 99.51 | 24.71 |
| 214 | 99.71 | 24.48 |
| 239 | 99.83 | 24.28 |
| 259 | 99.63 | 24.09 |

TABLE 6

| Temperature (°C.) | 400 | 450 | 475 | 500 |
|---|---|---|---|---|
| Conversion of R-134a (%) | 2.19 | 4.63 | 9.55 | 13.32 |
| Selectivity to TriFE (%) | 93.42 | 98.12 | 97.47 | 99.08 |

We claim:

1. A process for the production of trifluoroethylene which comprises passing a gaseous feed comprising 1,1,1,2-tetrafluoroethane and/or 1,1,2,2-tetrafluoroethane through a heated reaction zone in which there is contained a Lewis acid catalyst comprising chromia.

2. A process as claimed in claim 1 wherein the gaseous feed comprises 1,1,1,2-tetrafluoroethane.

3. A process as claimed in claim 1, wherein the chromia has been doped with a metal selected from the group consisting of nickel, cobalt, zinc, iron and copper.

4. A process as claimed in claim 3 wherein the metal is present in the form of a metal compound.

5. A process as claimed in claim 1 wherein the reaction zone is heated to a temperature in the range of from 350° to 800° C.

6. A process as claimed in claim 5 wherein the reaction zone is heated to a temperature in the range of from 400° to 600° C.

7. A process as claimed in claim 1 wherein the residence time for the 1,1,1,2-tetrafluoroethane and/or 1,1,2,2-tetrafluoroethane reactant in the reaction zone is in the range of from 0.1 to 7 seconds.

8. A process as claimed in claim 7 wherein the residence time for the 1,1,1,2-tetrafluoroethane and/or 1,1,2,2-tetrafluoroethane reactant in the reaction zone is in the range of from 0.3 to 5 seconds.

9. A process as claimed in claim 1 wherein the gaseous feed entering the heated reaction zone additionally comprises an inert diluent gas or vapour.

10. A process as claimed in claim 9 wherein the inert diluent is nitrogen.

11. A process as claimed in claim 9 or claim 10 wherein the volume ratio of the diluent to the 1,1,1,2-tetrafluoroethane and/or 1,1,2,2-tetrafluoroethane reactant in the gaseous feed entering the reaction zone is in the range of from 1:1 to 20:1.

12. A process as claimed in claim 9 or claim 10 wherein the volume ratio of the diluent to the 1,1,1,2-tetrafluoroethane and/or 1,1,2,2-tetrafluoroethane reactant in the gaseous feed entering the reaction zone is in the range of from 2:1 to 9:1.

13. A process as claimed in claim 12 wherein the volume ratio of the diluent to the 1,1,1,2-tetrafluoroethane and/or 1,1,2,2-tetrafluoroethane reactant in the gaseous feed entering the reaction zone is in the range of from 4:1 to 9:1.

14. A process as claimed in claim 1 which is operated at atmospheric pressure or substantially atmospheric pressure.

* * * * *